United States Patent [19]

Roberie

[11] Patent Number: 5,312,792
[45] Date of Patent: May 17, 1994

[54] CATALYTIC COMPOSITIONS

[75] Inventor: Terry G. Roberie, Ellicot City, Md.

[73] Assignee: W. R. Grace & Co.-Conn., New York, N.Y.

[21] Appl. No.: 916,460

[22] Filed: Jul. 20, 1992

Related U.S. Application Data

[63] Continuation of Ser. No. 593,834, Oct. 5, 1990, abandoned.

[51] Int. Cl.$^5$ ............................................. B01J 29/08
[52] U.S. Cl. ........................................ 502/60; 502/79
[58] Field of Search .................... 502/60, 79; 208/114

[56] References Cited

U.S. PATENT DOCUMENTS

| | | | |
|---|---|---|---|
| 3,354,096 | 11/1967 | Young | 252/435 |
| 4,115,424 | 9/1978 | Unland et al. | 252/432 |
| 4,259,212 | 3/1981 | Gladrow et al. | 252/455 Z |
| 4,340,465 | 7/1982 | Miller et al. | 208/120 |
| 4,357,265 | 11/1982 | Chiang | 252/455 Z |
| 4,431,517 | 2/1984 | Nevitt et al. | 208/111 |
| 4,454,241 | 6/1984 | Pine et al. | 502/68 |
| 4,465,780 | 8/1984 | Pine | 502/68 |
| 4,483,764 | 11/1984 | Hensley, Jr. et al. | 208/111 |
| 4,498,975 | 2/1985 | Pine et al. | 208/114 |
| 4,504,382 | 3/1985 | Pine | 208/114 |
| 4,567,152 | 1/1986 | Pine | 502/64 |
| 4,584,091 | 4/1986 | Pine | 208/114 |
| 4,765,884 | 8/1988 | Walker et al. | 208/89 |
| 4,839,319 | 6/1989 | Schuette et al. | 502/79 |
| 4,970,183 | 11/1990 | Nakamoto et al. | 502/68 |
| 5,110,776 | 5/1992 | Chitnis et al. | 208/114 |

FOREIGN PATENT DOCUMENTS

| | | |
|---|---|---|
| 0095364 | 10/1986 | European Pat. Off. . |
| 0252761 | 1/1988 | European Pat. Off. . |
| 0479485 | 4/1976 | U.S.S.R. . |

Primary Examiner—Carl F. Dees
Attorney, Agent, or Firm—Arthur P. Savage

[57] ABSTRACT

Crystalline aluminosilicate zeolite Y which contains phosphorus and its use in the preparation of hydrocarbon conversion catalysts.

8 Claims, No Drawings

CATALYTIC COMPOSITIONS

This is a continuation of application Ser. No. 593,834, filed Oct. 5, 1990 (now abandoned).

The present invention relates to catalytically active zeolites, and more specifically to phosphorus/zeolite Y compositions which are active for the conversion of hydrocarbons.

Crystalline aluminosilicate zeolites, particularly synthetic faujasite, i.e. zeolite Y, have been widely used in the preparation of hydrocarbon conversion catalysts, such as catalytic cracking and hydrocracking catalysts.

Thermally and chemically modified Y-zeolites, such as ultrastable Y zeolite (USY) and calcined rare-earth exchanged Y zeolite (CREY) are included in many commercial hydrocarbon conversion catalysts that are used to convert heavy hydrocarbon feedstocks into more valuable products such as gasoline and diesel fuel.

More recently, Y-zeolite catalysts which include phosphorus or phosphorus compounds have been described in the patent literature.

EP 095 364 B1 discloses catalytic cracking catalysts that contain clay based and synthetic Y-zeolites which are modified by the addition of phosphorus to enhance catalytic activity for the conversion of hydrocarbon feedstocks.

EP 0 252 761 A2 discloses cracking catalysts that contain a pretreated phosphorus/ultrastably Y zeolite.

It is an object of the present invention to provide novel phosphorus containing Y-zeolite compositions.

It is another object to provide phosphorus containing Y-zeolites that may be readily converted into highly active phosphorus/ultrastable-Y hydrocarbon conversion catalysts.

It is a further object to provide an economic method by which phosphorus modified ultrastable-Y zeolite containing catalysts may be manufactured and used on a commercial scale.

These and still further objects will become readily apparent to one skilled-in-the-art from the following detailed description and specific examples.

Broadly, my invention contemplates the preparation of phosphorus modified Y-zeolites wherein a partially hydrogen, ammonium exchanged sodium Y zeolite (Na, H, NH$_4$Y) is combined with a phosphorus compound such as phosphoric acid NH$_4$H$_2$PO$_4$, (NH$_4$)$_2$HPO$_4$ and NaH$_2$PO$_4$ to obtain a novel phosphorus containing zeolite-Y composition that may be readily converted to phosphorus/ultrastable-Y zeolite (P/USY).

More specifically, I have found that highly active phosphorus/ultrastably-Y zeolites may be prepared by the following process:

1) A sodium Y-zeolite (NaY) having a unit cell dimension of about 24.63 to 24.72 Å is ion-exchanged and washed with an ammonium salt solution and water to obtain a partially exchanged Na, H, NH$_4$Y that contains 1.0 to 5.0, and preferably 2.5 to 4.5, weight percent Na$_2$O.

2) The Na, H, NH$_4$Y is then combined with an aqueous phosphorus solution such as phosphate acid at a pH of about 4 to 7, and dried at a temperature of 20° to 350° C., preferably spray dried, to obtain a novel phosphorus containing Na, H, NH$_4$Y zeolite (P/Na, H, NH$_4$Y) that contains about 0.1 to 4 and more preferably 0.7 to 2 weight percent phosphorus expressed as P$_2$O$_5$.

3) The P/Na, H, NH$_4$Y is then heated in the presence of steam (10 to 100%) at a temperature of 500 to 700° C. for 0.5 to 2 hours to obtain a P/USY zeolite having a unit cell of about 24.45 to 24.60 Å and preferably 24.52 to 24.58 Å.

The P/USY zeolite obtained by the above process is particularly active for the catalytic cracking of hydrocarbons when combined with an inorganic oxide matrix such as silica, alumina, silica-alumina sols and gel and clay in accordance with the teaching of U.S. Pat. Nos. 3,650,988, 3,867,308, 3,957,689, CA 967,136 and U.S. Pat. No. 4,458,023. It is also contemplated that the P/USY may be exchanged with metal cations such as rare-earths (Ce, La, etc.), as well as Group II, VI and VIII metals such as Ni, Cr and Mg.

In a particularly preferred embodiment the P/USY, obtained in 3) above is combined with inorganic oxide matrix components such as clay and silica/alumina-sol in an aqueous slurry, which is then spray dried, and washed to remove Na$_2$O.

It is contemplated that the steam calcination step may take place during the manufacturing process or during use of the catalyst in a catalytic conversion process, such as fluid catalytic cracking (FCC).

The catalyst compositions contemplated herein will contain 10 to 80 weight percent P/USY, 3 to 30 weight percent alumina, silica or silica sol/gel binder and the balance clay (preferably kaolin). In addition the catalysts may contain particulate alumina, acid/thermal modified clay, additional zeolites/molecular sieves such as ZSM-5, zeolite Beta, USY, CREY, ALPO and SAPO, as well as combustion/oxidation additives such as Pt and/or Pd, and SOx conversion control sorbents such as RE/Al$_2$O$_3$, particularly La/Al$_2$O$_3$ compositions.

The P/USY catalytic cracking compositions, when used under FCC reaction/regeneration conditions of 455° to 565° C./575° to 820° C. to crack hydrocarbon feedstocks such as gas oil, residual oil and mixtures thereof, are particularly selective for the production of gasoline fractions. In addition, the compositions of the present invention find use as catalysts for hydrocracking, isomerization, and hydroprocessing.

Having described the basic aspects of the invention, the following examples are given to illustrate particular embodiments.

EXAMPLE I

Preparation of Na, H, NH$_4$Y 20,000 g of NaY having a unit cell dimension of 24.65 Å was ion exchanged with a 10% solution of ammonium sulfate at 80° C. for one-half hour and washed free of sulfate. The procedure was repeated, after which the sieve was dried twelve hours at 110° C.

The resulting product had the following characteristics:

Chemical Analysis (Wt. %)

| | |
|---|---|
| SiO$_2$ | 71.37 |
| Al$_2$O$_3$ | 24.42 |
| Na$_2$O | 4.05 |
| TV | 26.71 |

Physical Properties

Unit Cell 24.70 Å

EXAMPLE II

Preparation of P/Na, H, NH$_4$Y 4757 g of the Na, H, NH$_4$Y obtained in Example I was added to 31285 g of water. To this was added 690 g of 20% H$_3$PO$_4$. The resulting mixture having a pH of 4.7 was thoroughly agitated and spray dried using a gas inlet temperature of 316° C. and a gas outlet temperature of 149° C.

The resulting product had the following characteristics.

Chemical Analysis (Wt. %)

| | |
|---|---|
| SiO$_2$ | 71.41 |
| Al$_2$O$_3$ | 25.13 |
| P$_2$O$_5$ | 0.80 |
| Na$_2$O | 3.88 |
| TV | 25.26 |

Physical Properties

Unit Cell 24.70 Å

EXAMPLE III

Preparation of P/USY 5000 g of P/Na, H, NH$_4$Y of Example II was heated at 650° C. in the presence of 100% steam for 1 hour.

The resulting product had the following characteristics.

Chemical Analysis (Wt. %)

| | |
|---|---|
| SiO$_2$ | 71.41 |
| Al$_2$O$_3$ | 25.13 |
| P$_2$O$_5$ | 0.80 |
| Na$_2$O | 3.88 |

Physical Properties

Unit Cell 24.54 Å

EXAMPLE IV

Properties of FCC Catalyst from P/USY 3035 g of the P/USY obtained in Example III was combined with 944 g of alumina powder, 6000 g of silica-alumina sol, and 1347 g clay. The mixture was spray dried and the resulting catalyst washed to reduce the soda level. The catalyst was dried 150° to 175° C. for twelve hours before being steamed at 1500° F. (815° C.) for four hours and 1 atmosphere of steam partial pressure.

The resulting catalyst had the following properties.

Physical Properties

| | |
|---|---|
| Steamed as above | 174 m$^2$g |
| Fresh surface area (3 hrs. @ 1000° F.) | 285 m$^2$g |

EXAMPLE V

Evaluation of FCC Catalysts

Samples of catalysts prepared in Example IV were evaluated by using the procedure set forth by F. G. Ciapetta and D. S. Henderson, entitled "Microactivity Test for Cracking Catalysts", Oil and Gas Journal, Vol. 65, pages 89–93, Oct. 16, 1967 under the following conditions.

(a) Evaluation at constant Catalyst to Oil Ratio:

| | |
|---|---|
| Temperature | 980° F. |
| Catalyst/Oil Ratio | 4 |
| Feedstock | Sour Import Heavy Gas Oil |
| Space Velocity (WHSV$^{-1}$) | 30 |

The results are summarized in Table I below.

TABLE I

| Catalyst | Example IV | Control* |
|---|---|---|
| Conversion (wt. % of feed) | 71 | 62 |
| Gasoline C$_5$ + wt. % | 47.7 | 42.0 |
| LPG C$_1$ – C$_4$ wt. % | 20.3 | 17.4 |
| Coke wt. % | 2.9 | 2.3 |
| H$_2$ wt. % | 0.11 | 0.08 |

*Catalysts of Example V contain USY in lieu of P/USY.

(b) Evaluation at constant Conversion

The evaluation procedure of (a) was repeated at a constant conversion.

The results are summarized in Table II below.

TABLE II

The above Examples clearly indicate that valuable FCC catalysts may be obtained using the teachings of my invention.

I claim:

1. A method for preparing phosphorus-containing ultrastable Y-zeolite which comprises:
   (a) ion-exchanging and washing sodium Y zeolite having a unit cell dimension of about 24.53 to 24.72 Å with an ammonium salt solution and water to obtain a Y-zeolite which contains 1 to 5 weight percent Na$_2$O;
   (b) combining the washed Y-zeolite of step (a) with an aqueous solution of a phosphorus compound selected from the group consisting of H$_3$PO$_4$, NH$_4$ H$_2$ PO$_4$, (NH$_4$)$_2$ HPO$_4$, and Na H$_2$ PO$_4$ to obtain a Y-zeolite that contains about 0.1 to 5 weight percent P$_2$O$_5$;
   (c) heating the phosphorus-containing Y-zeolite of step (b) in the presence of steam to obtain a phosphorus-containing ultrastable Y-zeolite having au nit cell dimension of about 24.45 to 24.60 Å; and
   (d) washing the phosphorus-containing ultrastable Y-zeolite of step (c) to remove sodium ions.

2. The method of claim 1 wherein the Y-zeolite of step (b) is heated at a temperature of 500° to 750° C. in the presence of 10 to 100 percent steam.

3. The method of claim 1 wherein the phosphorus-containing ultrastable Y-zeolite of step (d) contains 0.7 to 2.0 weight percent P$_2$O$_5$.

4. The method of claim 1 wherein the product of step (b) is spray dried.

5. The method of claim 1 wherein the phosphorus compound is H$_3$PO$_4$.

6. The method of claim 1 wherein the phosphorus-containing ultrastable Y-zeolite obtained in step (c) has a unit cell dimension of 24.52 to 24.58 Å.

7. The method of claim 1 wherein the phosphorus-containing ultrastable Y-zeolite obtained in step (c) is combined with inorganic oxide matrix components selected from the group consisting of clay, silica, alumina, silica/alumina sol and mixtures thereof, spray dried and washed to obtain a fluid catalytic cracking catalyst.

8. The phosphorus-containing ultrastable Y-zeolite prepared by the method of claim 1.

* * * * *